(12) United States Patent
Teucher et al.

(10) Patent No.: US 9,446,204 B2
(45) Date of Patent: Sep. 20, 2016

(54) SAFETY DEVICE FOR AN INJECTION SYRINGE

(71) Applicants: Mark Digby Teucher, Bath (GB); Pascal Dugand, Estrablin (FR); Loïc Sebileau, Saint Priest (FR); Daniel Peter, Niederwangen (CH); Maxime Gaillot, Zaessingue (FR); Jürg Liniger, Ostermundigen (CH)

(72) Inventors: Mark Digby Teucher, Bath (GB); Pascal Dugand, Estrablin (FR); Loïc Sebileau, Saint Priest (FR); Daniel Peter, Niederwangen (CH); Maxime Gaillot, Zaessingue (FR); Jürg Liniger, Ostermundigen (CH)

(73) Assignee: HOFFMAN-LA ROCHE INC., Nutley, NJ (US)

( * ) Notice: Subject to any disclaimer, the term of this patent is extended or adjusted under 35 U.S.C. 154(b) by 129 days.

(21) Appl. No.: 14/148,115

(22) Filed: Jan. 6, 2014

(65) Prior Publication Data

US 2014/0194828 A1 Jul. 10, 2014

(30) Foreign Application Priority Data

Jan. 7, 2013 (EP) .................................... 13305010

(51) Int. Cl.
*A61M 5/32* (2006.01)
*A61M 5/315* (2006.01)

(52) U.S. Cl.
CPC .......... *A61M 5/326* (2013.01); *A61M 5/31511* (2013.01); *A61M 2005/3261* (2013.01)

(58) Field of Classification Search
CPC ............. A61M 5/326; A61M 5/2033; A61M 2005/206; A61M 2005/2407; A61M 2005/3261

USPC ......................... 604/131–155, 197, 198, 263
See application file for complete search history.

(56) References Cited

U.S. PATENT DOCUMENTS

| | | | |
|---|---|---|---|
| 5,085,640 A * | 2/1992 | Gibbs | A61B 5/154 144/145.1 |
| 5,314,415 A | 5/1994 | Liebert et al. | |
| 5,562,626 A * | 10/1996 | Sanpietro | A61M 5/326 604/110 |
| 5,599,309 A * | 2/1997 | Marshall et al. | 604/136 |
| 2001/0005781 A1* | 6/2001 | Bergens et al. | 604/208 |
| 2002/0091361 A1* | 7/2002 | Rosoff | A61M 5/282 604/212 |
| 2003/0187402 A1* | 10/2003 | Doyle | A61M 5/3137 604/198 |
| 2004/0039337 A1* | 2/2004 | Letzing | 604/157 |
| 2006/0036216 A1 | 2/2006 | Rimlinger et al. | |

(Continued)

FOREIGN PATENT DOCUMENTS

FR 2 830 765 A1 4/2003
WO WO 2011/039226 A1 4/2011
WO WO 2011/135269 A1 11/2011

OTHER PUBLICATIONS

European Search Report issued in European Application No. EP 13 30 5010 issued May 15, 2013.

*Primary Examiner* — Gerald Landry, II
(74) *Attorney, Agent, or Firm* — Oliff PLC

(57) ABSTRACT

The invention relates to a safety device for an injection syringe, the injection syringe including a body having an injection needle fitted thereon, the device including a plunger rod including a distal plunger part slidably movable in the body of the syringe, and a proximal triggering part, configured to trigger the displacement of a protection sheath, from an injection position, wherein the needle is uncovered, towards a safety position, wherein the needle is covered by the sheath. The proximal triggering part is able to move relative to the distal plunger part once the distal plunger part is at the distal end of its stroke, to trigger the displacement of the protection sheath.

11 Claims, 5 Drawing Sheets

(56) References Cited

U.S. PATENT DOCUMENTS

| | | | |
|---|---|---|---|
| 2006/0052748 A1* | 3/2006 | Coelho | A61M 5/3216 604/110 |
| 2006/0167412 A1* | 7/2006 | Marshall | 604/110 |
| 2007/0088287 A1* | 4/2007 | Chevallier | 604/198 |
| 2009/0105663 A1* | 4/2009 | Brand | A61M 5/326 604/197 |
| 2009/0270803 A1* | 10/2009 | Brunel | A61M 5/326 604/110 |
| 2010/0036320 A1* | 2/2010 | Cox et al. | 604/135 |
| 2010/0256570 A1* | 10/2010 | Maritan | A61M 5/2033 604/198 |
| 2011/0275992 A1* | 11/2011 | Abry et al. | 604/111 |
| 2011/0313364 A1* | 12/2011 | Rolfe et al. | 604/198 |
| 2011/0319864 A1* | 12/2011 | Beller | A61M 5/2033 604/506 |
| 2012/0220954 A1* | 8/2012 | Cowe | 604/228 |
| 2012/0283662 A1* | 11/2012 | MacDonald | A61M 5/24 604/236 |
| 2013/0053788 A1 | 2/2013 | Dugand et al. | |
| 2013/0317447 A1* | 11/2013 | Cowe | 604/196 |

* cited by examiner

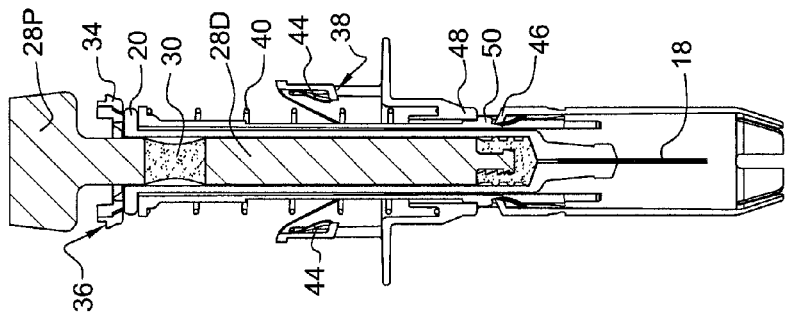
Fig. 4
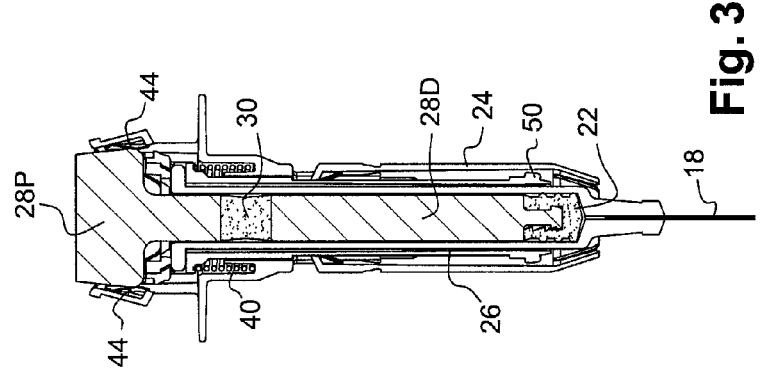
Fig. 3
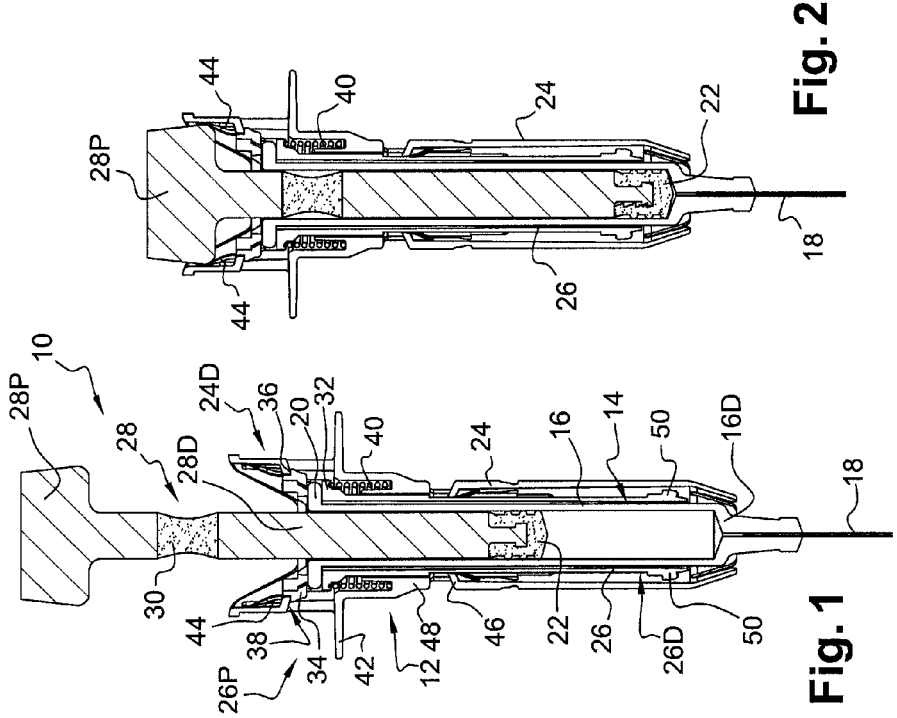
Fig. 2
Fig. 1

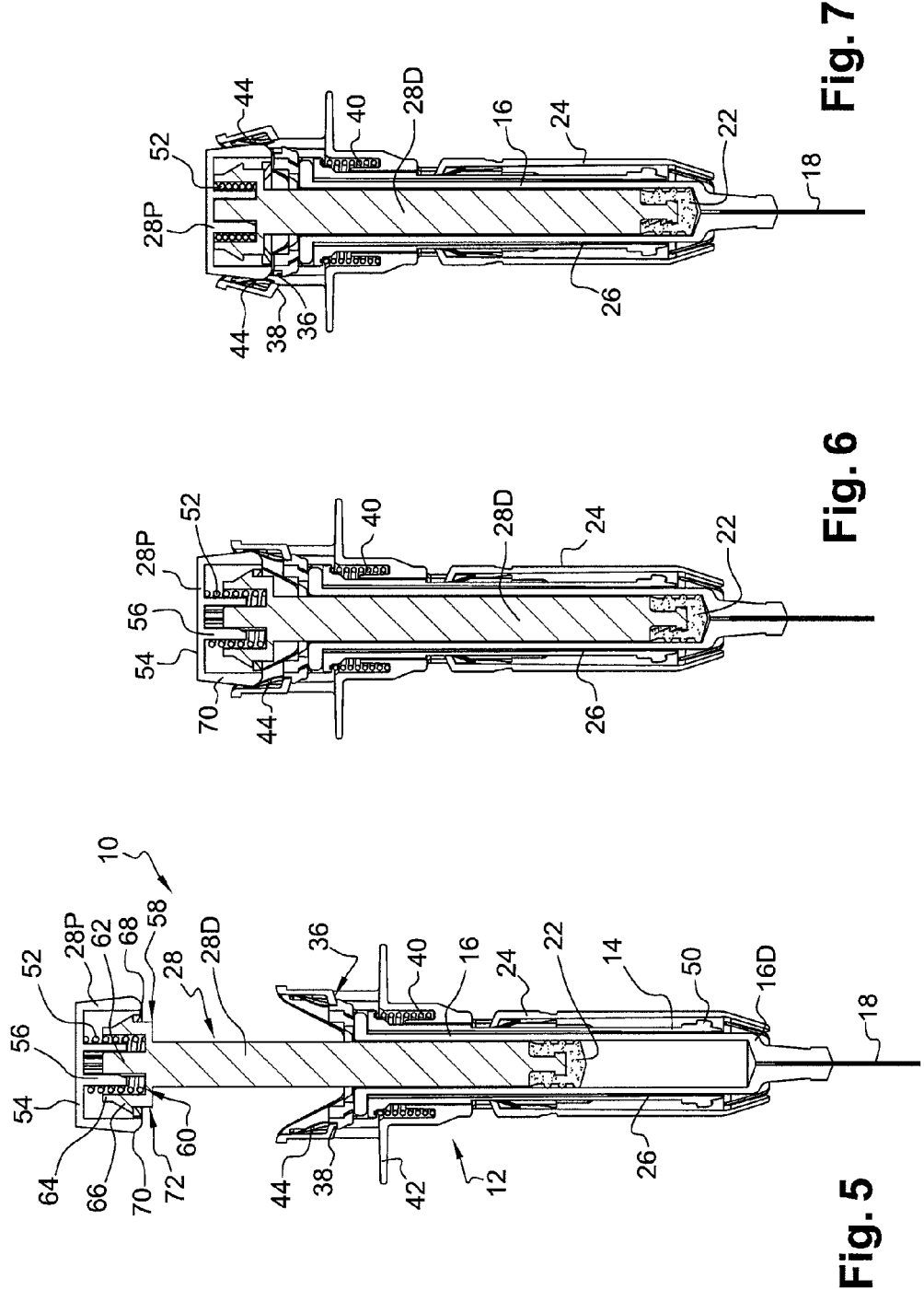

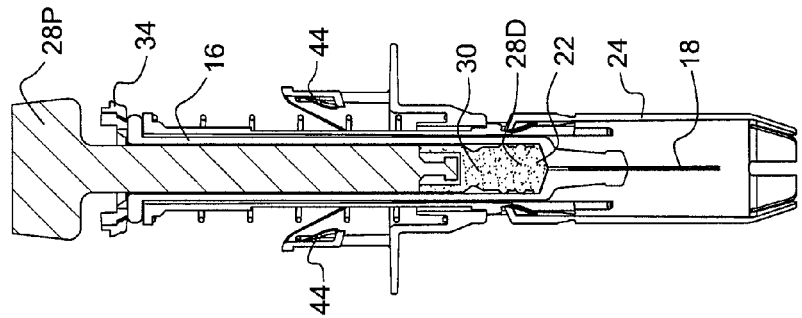
Fig. 11
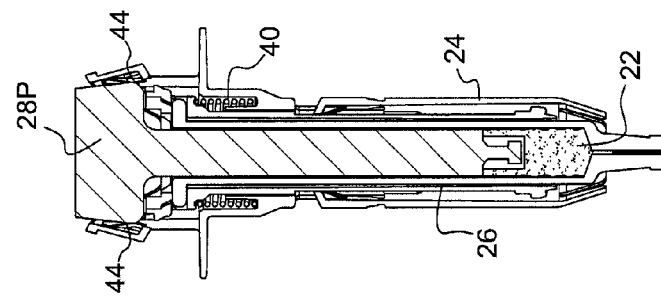
Fig. 10
Fig. 9
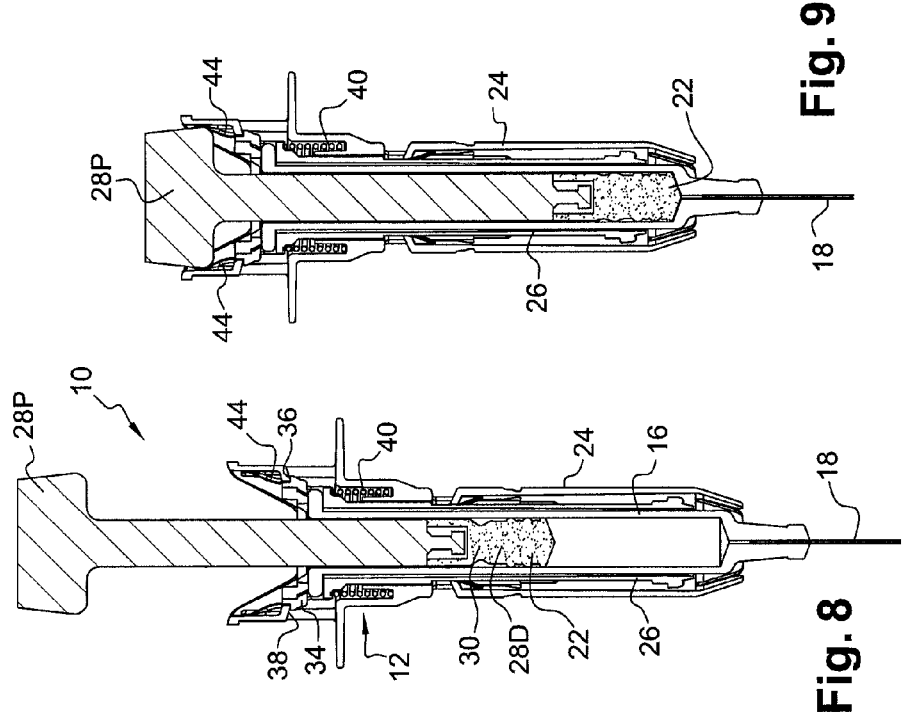
Fig. 8

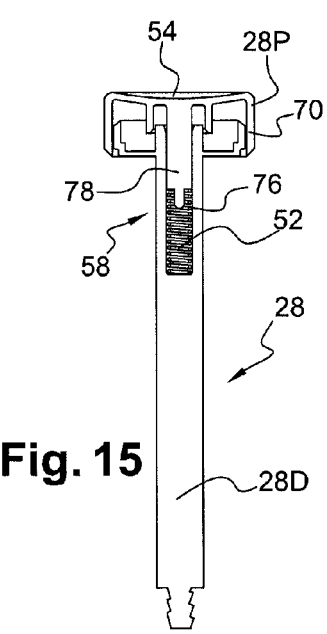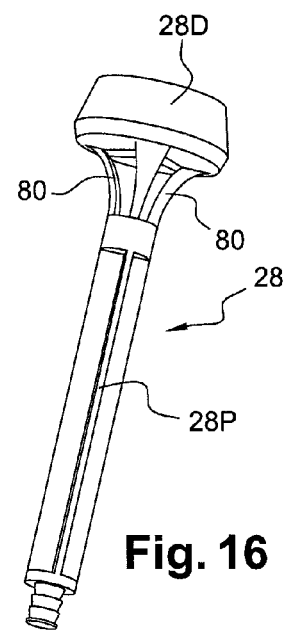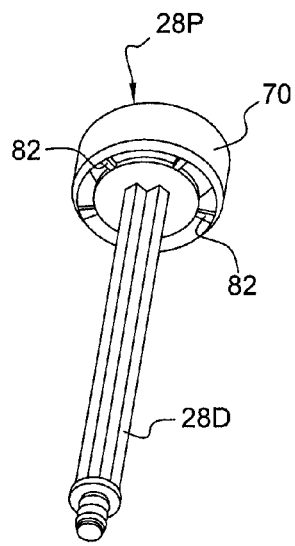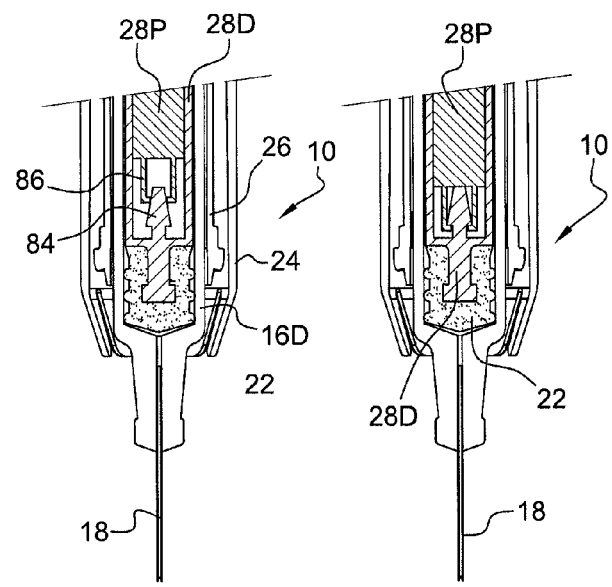

SAFETY DEVICE FOR AN INJECTION SYRINGE

The present invention relates to the field of safety device for a liquid injection syringe, in particular for a prefilled syringe.

A prefilled liquid injection syringe is known from the prior art. The syringe comprises a body of tubular shape forming a reservoir for the liquid and having fitted thereto at a distal end of the body a needle or a fitment for fastening a needle carrier on the syringe body. The syringe also includes a piston sealingly movable in the syringe body. Usually, the piston is a rubber part.

A safety device for a syringe such as the one described above is also known, for example from EP 1436026. The safety device comprises a syringe support, having a tubular shape, and being coaxial with the syringe body and a protective sheath also having a tubular shape, the protective sheath and the syringe support being axially movable relative to each other. The syringe support is housed in the protective sheath and is substantially coaxial therewith. The safety device also includes a plunger rod, intended to be fastened on the piston of the syringe. The rod is configured to trigger the displacement of the protective sheath relative to the syringe support from an injection position, wherein the needle is uncovered, towards a safety position, wherein the needle is covered by the sheath. The safety device enables the needle to be retracted automatically into the sheath so as to ensure that a person handling the syringe assembly cannot accidentally be pricked by the needle after the liquid has been injected into the body of a patient. This type of safety device is also called "passive" safety device.

The term "proximal" will be used to name an element or an end of an element that is axially closer to the end of the plunger rod that is to be actuated by a user than a "distal" end of an element. Thus, the term "distal" will be used to name an element intended to be axially closer to the needle.

However, the displacement of the sheath relative to the support or the syringe, i.e., to the needle, always occurs when the piston is near the distal end of the body of the syringe in an end-of-liquid injection position.

Yet, in some case, it can be of interest that the displacement of the sheath relative to the support does not take place automatically when the piston reaches the end-of-liquid injection position.

For example, in case of extemporaneous injection, i.e., when the liquid to be injected needs first to be reconstituted by mixing a solvent contained in the prefilled syringe body with an active ingredient contained in a vial, it is of interest that at the end of the injection of the solvent in the vial, the displacement of the protective sheath relative to the support would not be triggered. Indeed, the syringe needs to be refilled with the desired volume of the mixture before injection into the patient body. It is only at the end of this second injection that the safety device needs to be triggered so as to avoid any risk of contamination by a needle prick.

Moreover, especially with glass syringes, where large manufacturing tolerances are allowed, the safety device is activated near the end of the stroke of the proximal part of the plunger, generally while the plunger has not reached the distal end of the syringe body. This is detrimental to the ability to inject very small volume of liquid (in particular to inject medicine to babies or children) because when the user pushes the plunger to eliminated bubbles of air or to reduce the volume of liquid contained in the syringe body, the safety device can be activated and the medicine in the syringe cannot be injected anymore.

An object of the invention is to provide a safety device that is not always automatically triggered at the end of the piston stroke and that allows for full delivery of the product contained in the syringe body.

Accordingly, the invention provides a safety device for an injection syringe, the injection syringe comprising a body having an injection needle fitted thereon, the device being characterized in that the device comprises a plunger rod including:
- a distal plunger part slidably movable in the body of the syringe,
- a proximal triggering part, configured to trigger the displacement of a protection sheath, from an injection position, wherein the needle is uncovered, towards a safety position, wherein the needle is covered by the sheath, wherein the proximal triggering part is able to move relative to the distal plunger part once the distal plunger part is at the distal end of its stroke in order to trigger the displacement of the protection sheath.

Thanks to the fact that once the distal plunger part has reached the distal end of the syringe body, i.e. an end-of-injection position, the proximal triggering part is still able to move relative to the distal plunger part in the injection direction, the user is capable of choosing whether or not the safety device will be triggered. It is to be understood that the plunger rod may or may not comprise the piston.

If the user does not want to activate the safety device, once the distal plunger part reaches a stop at the distal end of its stroke, i.e., when a distal surface of a piston fitted on the distal plunger part or when a distal surface of the distal plunger part reaches its final distal position, the user does not exert more pressure on the proximal triggering part of the plunger. On the contrary, if the needle needs to be covered by the sheath after injection, once the piston has reached the distal end of the syringe, the user exerts more pressure on the proximal triggering part of the plunger rod which moves relative to the distal plunger part to trigger the displacement of the protection sheath from the injection position towards the safety position. This type of safety device is also called "active" safety device.

An advantage of the on-demand activation of the safety device is that it allows to complete delivery of the liquid contained in the syringe body as the displacement of the sheath can only be triggered once the distal plunger part has reached the distal end of the syringe body. For example, in case of extemporaneous injection, all the solvent contained in the prefilled syringe is injected in the vial and the concentration reproducibility of the active ingredient in the solution is therefore improved.

This is also advantageous when injecting a very small volume of liquid. As the piston is allowed to reach the distal end of the syringe body, even when the volume to be injected is small, e.g., when the piston stroke is around few millimeters (mm), preferentially less than 5 mm, more preferably less than 3 mm, one can reliably control the delivered volume of liquid and, if needed, can trigger the safety device at the end of the injection. This is particularly advantageous for the delivery medicine to a child or a baby. Indeed, one can then use a standard prefilled syringe, wherein the beginning of the dose is thrown away, so that there is only a small amount of medicine left in the syringe body. The risk to trigger the safety device during the reduction of the volume of liquid contained in the syringe body and before injecting the liquid to the patient is therefore reduced. In such a case, the complete delivery of the small amount of medicine is crucial, and the proposed safety device permits to be sure that the piston on the syringe reaches the end of its stroke without automatically triggering the protection sheath of the needle.

Another advantage is that the safety device can easily be transformed from "passive" to "active" by changing only the plunger rod, all the other element of the safety device remaining the same. This improves the standardization of the safety device. The choice to use a passive or an active safety device is made by the company selling the prefilled syringes.

It is to be noted that, usually, the plunger rod belongs to the safety device, whereas the piston, mounted on the distal plunger part of the plunger rod belongs to the prefilled syringe though, in some embodiments, the plunger rod comprises the piston. Usually also, the prefilled syringe is inserted into a syringe support, slidably mounted on or in the protection sheath. Furthermore, the piston is preferably made of rubber.

The safety device may also include at least one of the following characteristics, taken alone or in combination.

The distal plunger part and the proximal triggering part are linked by deformable means, deformable under a force that is higher than the force required to move a piston in the syringe body, when injecting the liquid contained in the syringe body. Therefore, under the force exerted to move the piston in the syringe body, the deformable means are slightly deformed but the deformation is not great enough to allow the safety device to be activated as soon as the piston is in contact with a distal end of the syringe body, i.e., when the distal plunger part has reached the end of its stroke. Thus, the force required to displace the proximal part relative to the distal part of the plunger rod on a distance allowing the triggering of the safety sheath is higher than the force required during injection to move the piston in the syringe body and the user can therefore choose if the safety device needs to be activated at the end of the distal plunger part stroke.

The deformable means comprise elastic means. The force applied on the plunger rod can be high at the beginning of the injection, as the piston can stick to the walls of the syringe body. The force may be higher than the force requested at the end of the injection to activate the safety device. It is therefore advantageous for the deformable means to be elastic. After the beginning of the injection, when the force applied to the plunger rod decreases to a normal injection force, the deformable means can resume a shape close to their initial shape. Even if the deformable means are slightly deformed at the end of the injection, the deformation is not great enough to allow the safety device to be automatically activated as soon as the distal surface of the piston is in contact with a distal end of the syringe body.

The elastic means comprise an elastomeric material glued, soldered, snap-fitted or overmolded on the distal plunger part and/or the proximal triggering part.

The elastic means are integral with the piston.

The elastic means is a spring. In such a case, the spring can be situated in the proximal part of the piston rod, the triggering part being supported by an element shaped like a cap, and the distal plunger part being supported by another tubular element.

The distal plunger part and the proximal triggering part each form a seat for the spring.

The distal plunger part and the proximal triggering part are snap-fastened to each other.

The distal plunger part and the proximal triggering part each comprise complementary anti-rotational means. Thus, the proximal part and the distal part cannot rotate relative to each other. The screwing of the plunger rod on the piston is therefore easier.

The complementary anti-rotational means comprise a lug cooperating with a groove.

The invention also provides an assembly of a safety device according to the invention and of a liquid injection syringe. This syringe is usually prefilled.

BRIEF DESCRIPTION OF DRAWINGS

These and additional objects, embodiments, and aspects of the invention will become apparent by reference to the figures and detailed description below in which:

FIG. 1 is an axial sectional view of a first embodiment of an assembly of a syringe and a safety device before injection;

FIG. 2 is an axial sectional view of the assembly of FIG. 1 at the end of the injection, before activation of the safety device;

FIG. 3 is an axial sectional view of the assembly of FIG. 1 during activation of the safety device;

FIG. 4 is an axial sectional view of the assembly of FIG. 1, the safety device being locked in safety position;

FIG. 5 is an axial section view of a second embodiment of an assembly of a syringe and a safety device before injection, before injection;

FIG. 6 is an axial section view of the assembly of FIG. 5 at the end of the injection, before activation of the safety device;

FIG. 7 is an axial section view of the assembly of FIG. 5 during activation of the safety device;

FIGS. 8 to 11 are axial sectional views of a third embodiment of an assembly of a syringe and a safety device, respectively before injection, before activation of the safety device, during activation of the safety device and locked in safety position;

FIG. 15 is a perspective view of a plunger rod according to a fifth embodiment;

FIG. 16 is an axial section view of a plunger rod according to a sixth embodiment;

FIG. 17 is a perspective view of a plunger rod according to a seventh embodiment;

FIGS. 18 and 19 are partial axial section views of an eighth embodiment of an assembly of a syringe and a safety device, respectively before activation of the safety device and during activation of the safety device.

Figure 12:
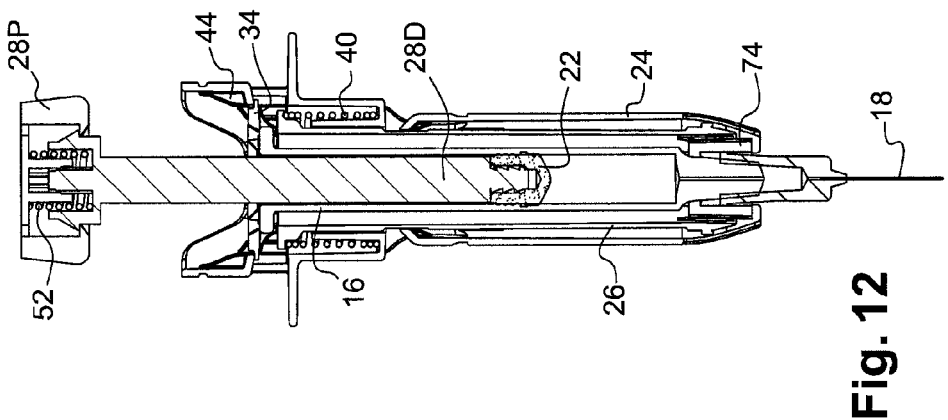
FIGS. 12 to 14 are axial section views of a fourth embodiment of an assembly of a syringe and a safety device, respectively before injection, before activation of the safety device and during activation of the safety device.

The present invention will now be described with reference to the specific embodiments of the invention. This invention may, however, be embodied in different forms and should not be construed as limited to the embodiments set forth herein. Rather, these embodiments are provided so that this disclosure will be thorough and complete, and to fully convey the scope of the invention to those skilled in the art.

A preferred embodiment of an assembly 10 of a safety device 12 and a prefilled injection syringe 14 is shown in FIGS. 1 to 4.

In FIG. 1, the syringe 14 comprises a tubular syringe body 16 forming a reservoir for the liquid. The body 16 has an open proximal end 16P provided with a collar 20, and a distal end 16D, generally in the form of a cone converging away from the proximal end 16P, having an injection needle 18 fitted thereon. For example the syringe body 16 is made of glass material, it could also be made of plastic material.

The syringe 14 also includes a piston 22 mounted to be sealingly and axially movable in the body 16 from a ready-to-inject position, shown in FIG. 1, to an end-of-injection position, shown in FIG. 2, in which the piston 22 is in contact with the distal end 16D of the body 16.

The safety device 12 comprises the first member of generally tubular shape, referred to as the protective sheath 24, and a second member of generally tubular shape, referred to as the syringe support 26. The support 26 is housed inside the sheath 24, being substantially coaxial therewith. For example, the sheath 24 and the support 26 are made of plastic material.

The sheath 24 and a support 26 are movable axially relative to each other between an injection position, wherein the needle 18 is uncovered, and a safety position, wherein the needle 18 is covered by the sheath 24. The sheath 24 also comprises grip means including, in this embodiment, two outer radial tabs 42. The sheath 24 is locked in the injection position thanks to complementary retaining means 36, 38 respectively carried by the support 26 and sheath 24. These retaining means oppose the resilient return force of the thrust spring 40. The first retaining means 38 are formed by the free end of an axial tongue 44 provided on a proximal end 24D of the sheath 24. The tongue 44 is elastically deformable in a radial direction. The second retaining means 36 are formed on a proximal part 26P of the syringe support 26.

The safety device also has locking means for locking the sheath in the safety position as shown in FIG. 4. The locking means comprise at least one radial projection 50 formed on a distal end 26D of the syringe support 26 for snap-fastening between a pair of abutments 46, 48 formed on the sheath 24, to prevent axial movement of the sheath 24 relative to the support 26 and therefore to the needle 18.

The safety device 12 also comprises a plunger rod 28, for example made of plastic material. The plunger rod 28 comprises a distal plunger part 28D and a proximal triggering part 28P. The distal part 28D and the proximal part 28P are linked by deformable means, which in this embodiment are elastic means comprising and elastomeric material 30 glued, soldered, snap-fitted or overmolded on the distal part 28D and on the proximal part 28P. The proximal part 28P is configured to trigger the displacement of the sheath 26 from the injection position to the safety position.

In this embodiment, the elastomeric material 30 has a non-constant section along the axial axis of the plunger rod 28, the middle section being smaller than the end sections. The plunger rod 28 is mounted on the piston 22, for example by screwing the plunger rod 28 on the piston 22.

The body of this syringe 14 is housed in a known manner in the support 26. More particularly, the syringe body 16 is prevented from moving axially in this syringe support 26 as the collar 20 is snap-fastened between appearing seat 32 formed in the support 26 and at least one retractable locking abutment 34 secured to the support 26, in this embodiment, the support 26 has two diametrically opposite locking abutment 34.

With references to FIGS. 1 to 4, the operation of the assembly 10 will be described.

Once the prefilled syringe body 16 is mounted in the safety device 12 and the plunger rod 18 is screwed on the piston 22, the assembly 10 is in the injection position and ready to use.

The user take the assembly 10 in one hand putting two fingers on the outer radial tabs 42 and one finger on our the proximal part 28P of the piston rod. The user then exerts on the plunger rod 18 until the distal part 28D reaches the end of its stroke and the piston 22 is in contact with the distal end 16D of the syringe body 16, as can be seen in FIG. 2. In this position, the proximal part 28P of the plunger rod 18 has not yet reached the end of its stroke.

If the user wants to activate the safety device 12, a force higher than the force used to move the plunger in the syringe body 16 is needed to deform the elastomeric material 30, in this example axially and radially, as shown in FIG. 3, and to allow proximal part 28P to cooperate with the tongue 44 deforming the tongue 44 radially and unlocking the retaining means 36 and 38. As described, the proximal part 28P of the plunger rod is configured to trigger the displacement of the sheath 24 from its injection position towards its safety position, the displacement being relative to the support 26. To this end, the proximal part 28P has an external diameter that is larger than the internal diameter of the tongues 44. When the proximal part 28P reaches the tongues 44, the proximal part 28P pushes aside and deforms radially the tongues 44 causing the first and second retaining means 38, 36 to disengage. There is therefore no more force opposing the spring 40 to detent. The safety device 12 is activated while the proximal part 28P of the plunger rod 28 has reached the end of its stroke.

Driven by the spring 40, the displacement of the sheath 24 relative to the support 26 is triggered and the sheath takes its safety position, as shown in FIG. 4. It can be seen that the sheath 24 and the support 26 are locked in the safety position thanks to the snap-fastening of two projections 50, each between a pair of abutments 46, 48.

If the user does not want to activate the safety device 12, once the distal part 28D of the plunger rod 28 has reached the end of its stroke, the user does not apply a supplementary force on the proximal part 28P of the plunger rod, although the piston 22 having reached the distal end 16D of the syringe body, the safety device is not activated and the assembly the syringe can be filled, for example with a reconstituted mixture.

In the embodiment shown in FIGS. 8 to 11, wherein the elements common to embodiment of FIGS. 1 to 4 are identified by same numeral references, the plunger rod 28, and more particularly the distal plunger part 28D, comprises the piston 22. In this example, the elastomeric material 30 is integral with the piston 22. It could also be glued, soldered, snap-fitted or overmolded on the distal plunger part 28D.

The operation of the assembly 10 is similar to the one described above. Once the piston 22, i.e., the distal part 28D of the plunger rod has reached the end of its stroke, as shown in FIG. 9, when the user wants to activate the safety device 12, a force higher than the force used to move the plunger in the syringe body 16 is needed to deform the elastomeric material 30, in this example axially and radially, as shown in FIG. 10, and to allow proximal part 28P to cooperate with the tongue 44 deforming the tongue 44 radially and unlocking the retaining means 36 and 38. The deformation of the elastomeric material 30 allowing for displacement of the proximal triggering part 28P relative to the distal part 28D so the proximal part 28P reaches the end of its stroke.

In another preferred embodiment shown in FIGS. 5 to 7, elements common to embodiment of FIGS. 1 to 4 are identified by same numeral references.

The safety device 12 and the syringe 14 are similar to the ones described in the previous embodiment except for the plunger rod 28.

In the embodiment of FIGS. 5 to 7, the plunger rod 28 comprises the distal plunger part 28D screwed on the piston 22 and a proximal part 28P linked to the distal part by an activation spring 52.

The proximal triggering part 28P has a general form of a cap having an essentially flat bottom part 54 and an annular wall 70. The flat bottom part 54 carries an inner annular projection 56 helping to center the activation spring 52 within the proximal part 28P, the flat bottom part 54 forming a seat for the activation spring 52. The external diameter of the annular wall 70 is larger than the internal diameter of the tongues 44.

The distal end 28D comprises, at its proximal end 58, a groove 60 for receiving the activation spring 52. The groove 60 is formed by an external annular wall 64 and an inner cylindrical projection 62, the cylindrical projection 62 being housed in sliding contact in the annular projection 56.

The proximal part 28P and the distal part 28D comprise complementary snap-fastening means 66, 68. The snap-fastening means are formed, on the one hand, by a bead 66 supported by an external surface of the external annular wall 64 of the proximal end 58 of the distal part 28D, and on the other hand, by lugs 68 supported by an inner surface of the annular wall 70 of the proximal part 28P. Once the activation spring 52 is placed within the cap-shaped proximal part 28P, around the inner annular projection 56, the proximal part is mounted on the distal part 28D. The activation spring 52 is in compression between the two parts 28P, 28D. The complementary snap-fastening means 66, 68, opposing the force of the activation spring 52, secure the distal part 28D and the proximal part 28P together.

The plunger rod 28 also comprises anti-rotational means to avoid rotation of the proximal part 28P relative to the distal part 28P. The anti-rotational means comprise, on the one hand, the lugs 68 supported by the inner surface of the annular wall 70 of the proximal part 28P and, on the other end, grooves 72 formed in the external annular wall 64. These anti-rotational 68, 72 means are complementary and cooperating with each other. It is to be noted that in this example, the lugs 68 are forming snap-fastening means as well as anti-rotational means. Thanks to these complementary anti-rotational means, screwing of the plunger rod 28 onto the piston is facilitated.

The operation of the assembly 10 is similar to the one described for the previous embodiment. Once the distal part 28P of the plunger rod 28 reaches the end of its stroke as shown in FIG. 6, i.e., when the piston 22 is in contact with the distal end 16D of the syringe body, the user can choose whether or not he wants to activate the safety device. The proximal part 28P of the plunger rod has not yet reached the end of its stroke.

If the safety device 12 needs to be activated, a complementary force applied on the proximal part 28P of the piston rod 28 is required so as to further compress the activation spring 52 and to bring the proximal part 28P in its end-of-stroke position, as shown in FIG. 7. Indeed, the force required to compress the activation spring 52 is greater than the force required to move the piston in the syringe body.

The external diameter of the annular wall 70 being larger than the inner diameter of the tongues 44, when the proximal part 28P reaches the tongues 44, the proximal part 28P pushes aside and deforms radially the tongues 44 causing the first and second retaining means 38, 36 to disengage. There is therefore no more force opposing the spring 40 to detent. The safety device 12 is activated while the proximal part 28P of the plunger rod 28 has reached the end of its stroke.

Driven by the spring 40, the displacement of the sheath 24 relative to the support 26 is triggered and the sheath takes its safety position, similarly to what has been previously described.

The plunger rod 28 of the embodiment shown in FIG. 15 is similar to the one of FIGS. 5 to 7. The proximal triggering part 28P has a general form of a cap having an essentially flat bottom part 54, an annular wall 70 and an inner cylindrical projection 78. The activation spring 52 is received in a room 76 housed in the proximal end 58 of the distal part 28D of the plunger rod and the inner cylindrical projection 78 is slidably movable in the room 76, so as to compress the activation spring 52 upon activation of the safety device.

Figure 13:
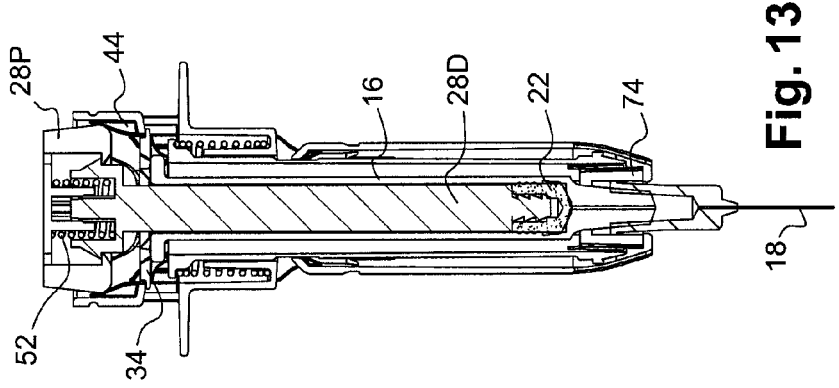
Figure 14:
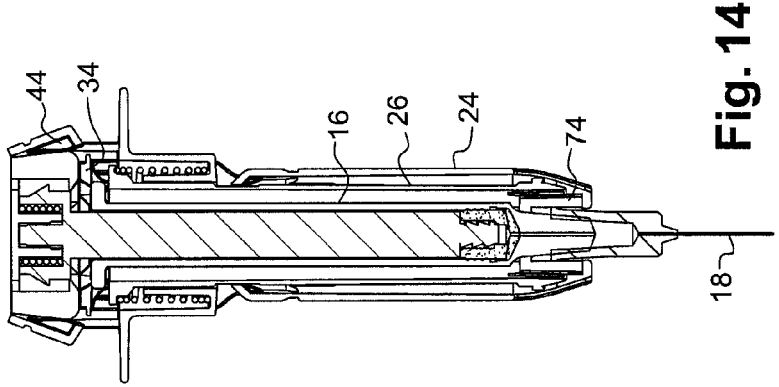

FIGS. 12 to 14 show another embodiment, similar to the embodiment of FIGS. 5 to 7 in which the needle 18 is mounted onto the syringe body 16 via a fastener end piece referred to as a Luer lock 74. Thanks to the Luer lock 74, the prefilled syringe can be stored without the needle mounted on the syringe body 16, with or without the safety device 12. Thus, during storage, the syringe is more compact.

The Luer lock also allows for changing the needle 18 carried by the syringe body 16. For example, in case of extemporaneous injection, a first needle is used to inject the solvent in the vial and to refill the syringe while a second needle, generally thinner, is used to inject the reconstituted mixture into the patient body.

In the embodiment shown in FIG. 16, the elastic means comprise elastic lugs connecting the distal part 28D to the proximal part 28P of the plunger rod 28.

Elastic deformation means have been described; however, the deformation means can also be plastic, the force required to plastically deform the deformation means, on a distance allowing to trigger the displacement of the sheath, being higher than the force required to move a piston in the syringe body.

As shown in FIG. 17, the proximal part 28P of the plunger rod 28 comprises a plurality of breakable links 82 between the proximal end 58 of the distal part 28D and the annular wall 70 of the proximal triggering part. When the piston 22 mounted on the distal end of the distal part 28D of the plunger rod 28 (not shown in FIG. 17) is in contact with the distal end 16D of the syringe body, the user can choose whether or not he wants to activate the safety device. The proximal part 28P of the plunger rod has not yet reached the end of its stroke. To activate the safety device, once the distal part 28D of the plunger rod 28 has reached the end of its stroke, the user needs to apply an additional force to break the breakable links to allow the proximal part 28P to reach the end of its stroke and to allow proximal part 28P to cooperate with the tongue 44 deforming the tongue 44 radially and unlocking the retaining means 36 and 38.

It is to be noted that the links 82, instead of being breakable, could also be deformable, elastically or plastically.

FIGS. 18 and 19 show an eighth embodiment of an assembly 10 of a syringe 14 and a safety device 12 in which the plunger rod 28 comprises a hollow cylindrical distal part 28D receiving the proximal triggering part 28P. The proximal part 28P is slidably movable in the distal part 28D. The hollow cylindrical distal part 28D carries a projection 84 on the distal end of its inner surface. In the embodiment of FIG. 18, the projection 84 has a cone shape which section decreases towards the proximal end of the device. The distal end of the proximal part 28P of the plunger rod 28 carries a deformable annular projection 86 that cooperates with the projection 84 carried on the inner surface of the distal part 28D. Upon injection, the annular projection 86 pushes the projection 84, the force required for injection being smaller the force required to deform the annular projection 86, both the proximal part 28P and the distal part 28D slide together in the body 16 of the syringe. When the piston 22 mounted on the distal end of the distal part 28D of the plunger rod 28 is in contact with the distal end 16D of the syringe body, the user can choose whether or not he wants to activate the safety device. The proximal part 28P of the plunger rod has not yet reached the end of its stroke. To activate the safety device, once the distal part 28D of the plunger rod 28 has reached the end of its stroke, the user needs to apply an additional force to deform the annular projection 86 to allow the projection 84 to be received in the annular projection 86. The proximal part 28P can therefore reach the end of its stroke and the proximal part 28P can cooperate with the tongue 44 deforming the tongue 44 radially and unlocking the retaining means 36 and 38.

It is to be noted that the elastic means can be prestressed to a given value, i.e., the elastic means will not deformed unless a force larger than the prestressed value is exerted on the triggering proximal part 28P of the plunger rod 28.

The stiffness of the thrust spring 40 may be adapted in function of the force required to activate the safety device.

The safety device can also operate without syringe support, the sheath being mounted onto the syringe body.

Some plunger rod may also comprise a sealing bead and there is therefore no need of a piston as described above. Thus, the end of the stroke of the plunger rod is reached when the distal plunger rod is in contact with the distal end of the syringe body.

The invention claimed is:

1. Safety device for an injection syringe, the injection syringe comprising a syringe body forming a reservoir for a liquid and having an injection needle fitted thereon, wherein the safety device comprises:
    a protective sheath and a syringe support slidably movable relative to each other, the syringe body being housed in the syringe support; and
    a plunger rod including:
        a distal plunger part slidably movable in the syringe body, and
        a proximal triggering part, configured to trigger a displacement of the protective sheath from an injection position, wherein the injection needle is uncovered, towards a safety position, wherein the injection needle is covered by the protective sheath,
        wherein the proximal triggering part is movable relative to the distal plunger part once the distal plunger part is at a distal end of its stroke in order to trigger the displacement of the protective sheath which thus moves to the safety position.

2. The safety device according to claim 1, wherein the distal plunger part and the proximal triggering part are linked by deformable means, the deformable means being deformable under a force that is higher than the force required to move a piston in the syringe body when injecting the liquid contained in the syringe body.

3. The safety device according to claim 2, wherein the deformable means comprise elastic means.

4. Safety device for an injection syringe, the injection syringe comprising a syringe body forming a reservoir for a liquid and having an injection needle fitted thereon, wherein the safety device comprises:
    a protective sheath and a syringe support slidably movable relative to each other, the syringe body being housed in the syringe support; and
    a plunger rod including:
        a distal plunger part slidably movable in the syringe body, and
        a proximal triggering part, configured to trigger a displacement of the protective sheath from an injection position, wherein the injection needle is uncovered, towards a safety position, wherein the injection needle is covered by the protective sheath,
        wherein the proximal triggering part is movable relative to the distal plunger part once the distal plunger part is at the distal end of its stroke in order to trigger the displacement of the protective sheath;
    wherein:
        the distal plunger part and the proximal triggering part are linked by deformable means, the deformable means being deformable under a force that is higher than the force required to move a piston in the syringe body when injecting the liquid contained in the syringe body;
        the deformable means comprise elastic means; and
        the elastic means are integral with the piston.

5. The safety device according to claim 3, wherein the elastic means comprise an elastomeric material glued, soldered, snap-fitted or overmolded on the distal plunger part and/or the proximal triggering part.

6. The safety device according to claim 3, wherein the elastic means is a spring.

7. The safety device according to claim 6, wherein the distal plunger part and the proximal triggering part each form a seat for the spring.

8. The safety device according to claim 7, wherein the distal plunger part and the proximal triggering part are snap-fastened to each other.

9. Safety device for an injection syringe, the injection syringe comprising a body having an injection needle fitted thereon, wherein the device comprises a plunger rod including:
    a distal plunger part slidably movable in the body of the syringe,
    a proximal triggering part, configured to trigger the displacement of a protection sheath from an injection position, wherein the needle is uncovered, towards a safety position, wherein the needle is covered by the sheath,
    wherein the proximal triggering part is able to move relative to the distal plunger part once the distal plunger part is at the distal end of its stroke in order to trigger the displacement of the protection sheath; and
    wherein the distal plunger part and the proximal triggering part each comprise complementary anti-rotational means.

10. The safety device according to claim 9, wherein the complementary anti-rotational means comprise a lug cooperating with a groove.

11. Assembly of the safety device according to claim 1 and of the injection syringe.

* * * * *